United States Patent [19]

Linden et al.

[11] Patent Number: 5,525,526
[45] Date of Patent: Jun. 11, 1996

[54] IMMUNOASSAY FOR INOSITOLS

[75] Inventors: Joel Linden, Charlottesville; Thomas Piccariello, Blacksburg; George Vandenhoff, Charlottesville, all of Va.

[73] Assignee: The University of Virginia Patent Foundation, Charlottesville, Va.

[21] Appl. No.: 191,259

[22] Filed: Feb. 2, 1994

[51] Int. Cl.$^6$ .................... G01N 33/545; G01N 33/534; G01N 33/535; C07K 16/44
[52] U.S. Cl. .................. 436/543; 435/7.92; 435/7.93; 436/531; 436/545; 436/815; 436/822; 530/389.8
[58] Field of Search .................. 530/389.8; 435/7.93, 435/7.92; 436/545, 531, 532, 815, 822, 543

[56] References Cited

U.S. PATENT DOCUMENTS

| | | | |
|---|---|---|---|
| 5,183,764 | 2/1993 | Kennington et al. | 435/811 |
| 5,252,707 | 10/1993 | Ozaki et al. | 530/345 |

FOREIGN PATENT DOCUMENTS

| | | |
|---|---|---|
| 477001 | 3/1990 | European Pat. Off. . |
| 2667945 | 4/1992 | France . |
| 168299 | 7/1989 | Japan . |

OTHER PUBLICATIONS

C. Jaffe et al., Experimental Parasitology, vol. 70, pp. 12–24 (1990).

R. Levy et al., J. Clin. Immunology, vol. 10, No. 3, pp. 141–145 (1990).

J. Fournie et al., J. Biol. Chem., vol. 266, No. 2, pp. 1211–1219 (1991).

J. Represa et al., Proc. Natl. Acad. Sci. USA, vol. 88, pp. 8016–8019 (1991).

Mitsui Pharmaceutical, Inc., English abstract of Japanese patent 1–168299, Jul. 1989.

W. Tegge et al., Carbohydrate Research, vol. 230, pp. 63–77 (1992).

B. Kohne et al., Chemical Abstract No. 105:144027y, Z Naturforsch, B: Anorg. Chem., Org. Chem. vol. 41B, No. 8, pp. 1036–1044 (1986).

E. Flithuth et al., Chemical Abstract No. 117:8325q, Chem. Phys. Lipids, vol. 160, No. 8, pp. 253–261 (1992).

B. Erlanger, Methods in Enzymology, vol. 70, pp. 85–105 (1980), Academic Press, Inc.

*Primary Examiner*—Mary E. Ceperley
*Attorney, Agent, or Firm*—William J. McNichol, Jr.; Janet Sleath

[57] ABSTRACT

Antibodies raised against derivatives of inositol are used to assay for specific isomers of inositol in a sample by first converting any inositol present in the sample to the derivative that was used to raise the antibody and then conducting an immunoassay for the inositol derivative in a conventional manner.

22 Claims, 6 Drawing Sheets

IMMUNOASSAY FOR INOSITOLS

BACKGROUND OF THE INVENTION

This invention relates to methods for assaying for the presence of the hexose sugar, inositol, and to methods for the production of antibodies to inositol derivatives. This invention provides quantitative assays for the various isomers of this compound.

Inositol is of interest in a number of biological systems. The D-chiro isomer of this compound has been shown to be useful both as an indicator of insulin resistant diabetes and as a therapeutic agent for this disorder. See, U.S. Pat. No. 5,124,360.

Myoinositol phosphates are known to be involved in the modulation of $Ca^{2+}$ homeostasis (Hughes, A. R. et al. Am. Rev. Resp. Dis. 141 (3 Pt 2) S115-8 (March, 1990)), have been implicated in the mechanism of malignant hypothermia (Scholz, J. et al. Br. J. Anesth. Vol. 66, pp. 692–6 (1991)) and have a significant role in many other physiological systems. Myoinositol phosphates can be quantified following their enzymatic conversion to myoinositol e.g. with alkaline phosphatase.

Direct chemical assays for inositol phosphates are known. However, these cannot distinguish between inositol isomers (optical techniques), lack sensitivity (gas chromatography and nuclear magnetic resonance), are very expensive (fast atom bombardment), or are specific for inositol-1,4,5-triphosphate (Palmer S. and Wakelam M. J. Biochimica Et Biophysica Acta. 1014(3):239–46, 1989).

Immunoassays per se have long been known. Unfortunately, such methods are not without their limitations. The success of an immunoassay rests upon the ability of an animal immune system to recognize a substance as foreign to the normal and to generate antibodies which are specific to the analyte of interest. Often, a compound of interest is simply too small to permit the animal immune system to recognize it as a foreign substance. Sometimes, the analyte is, in fact, not foreign at all. In still other cases, antibodies can be produced, but they are not very specific and cross react with compounds other than the analyte.

An analyte can sometimes be linked to a larger molecule so that the resulting conjugated compound is large enough to be recognized by the animal immune system as foreign. In this circumstance, when the analyte is linked to a large, relatively inert substance (such as bovine serum albumin), it is referred to as a hapten. The conjugated hapten is injected into an animal (such as a rabbit) with the hope that antibodies to the hapten will be produced and that they will be specific to the hapten. Unfortunately, attempts to use this technique to create an immunoassay for inositols have not been successful.

SUMMARY OF THE INVENTION

It has now been found that derivatized inositols can be used to inoculate animals and that animal immune systems will recognize this conjugate as foreign and produce antibodies to it. These antibodies may be used to perform sensitive immunoassays which are often capable of differentiating between the various isomers of inositol. The preferred derivatives of inositol are acetylated derivatives, although other derivatives such asacylated derivatives as well as derivatives obtained by formation of ethers, acetals, ketones and ketals may be used. It has also been found that complete derivatization of the inositol (e.g., acetylation of all of the inositol's OH groups save the one which is used to form the conjugate) is most preferred.

With antibodies produced in this manner, it is possible to assay for specific isomers of inositol in a sample by (1) subjecting the sample to derivatizing conditions so that inositol, if present in the sample, will be converted to a derivative such as was used to form the hapten and then (2) conducting an immunoassay for the inositol derivative in a conventional manner.

DETAILED DESCRIPTION OF THE INVENTION

Figure 1:
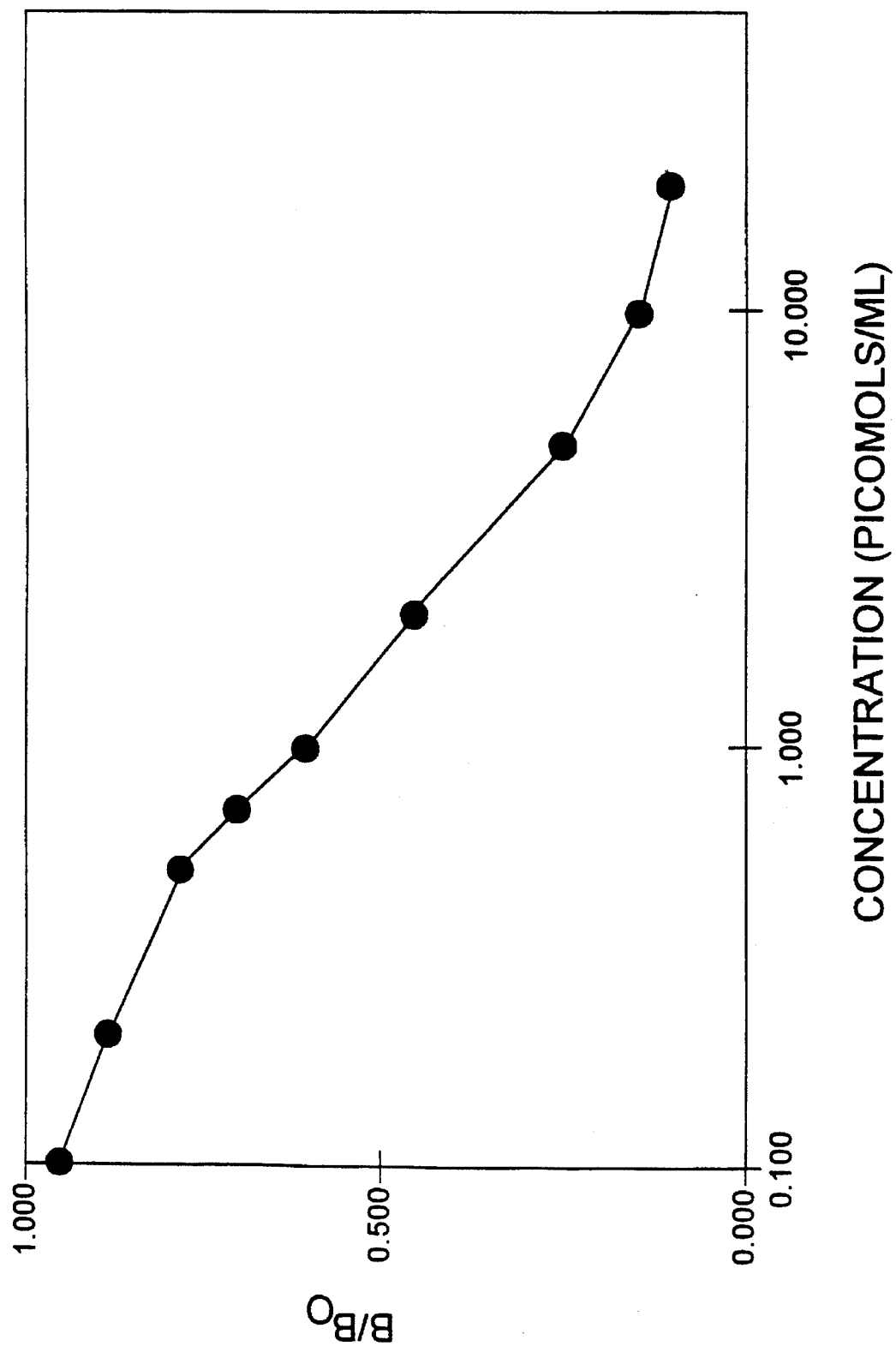
FIG. 1 is a standard assay curve for acetylated myoinositol.

It has been found that derivatives of inositol can be used as haptens to which antibodies can be raised. Acetylated derivatives are preferred.

The derivatized inositol is advantageously linked to bovine serum albumin (BSA), but other large molecules, such as purified protein derivative or hemocyanin may also be used. A variety of linkers may be used, including succinic acid, carboxylic acids, carboxylic anhydrides, pyruvic acids, levulinic acids, sulfhydryls or amines.

A suitable derivative of D-chiroinositol (DCI) was prepared and conjugated with BSA in the following manner:

Preparation of 1,2;3,4;5,6-tri-O-isopropylidene D-chiroinositol.

D-Chiroinositol (1.62 g) was stirred with dry dimethylformamide (10 ml), p-toluene sulfonic acid (86 mg) and dimethoxypropane (6.6 ml) at 60° C. for 15 hours. The solution was cooled to room temperature where 0.33 ml of triethylamine was added. The solution was diluted with 100 ml ether and washed with 4×90 ml $H_2O$, 20 ml brine, dried over sodium sulfate, filtered and the ether removed in vacuo. The residue was recrystallized from ether and petroleum ether to yield 1.74 g of product (64% yield).

Preparation of 1,2; 5,6-di-O-isopropylidene-D-chiroinositol 1,2;3,4;5,6-Tri-O-isopropylidene-D-chiroinositol (1.94 g) was stirred with 10 ml of 95% acetic acid at 55° C. for 8 hours. The solution was concentrated to dryness in vacuo at 50° C. The residue was recrystallized from methylene chloride and hexanes to yield 1.09 g (65% yield) product.

Preparation of 1,2;5,6-di-O-isopropylidene-D-chiroinositol-3-succinate 1,2;5,6-Di-O-isopropylidene-D-chiroinositol (245 mg) was mixed with 10 ml benzene and 247 mg of dibutyltin oxide in a Dean-Stark apparatus and refluxed for one hour.

The solution was cooled to room temperature where $10^6$ CPM's of [$^{14}$C] radiolabelled succinic anhydride was added and the solution stirred for an additional hour at which point 13 mg of succinic anhydride was added and the solution stirred for one more day. The mixture was dried in vacuo and the residue was loaded on a 2×20 cm flash column packed with silica gel 60 and the column was eluted with ether until the requisite compound was eluted from which the ether was removed in vacuo to yield 314 mg of product (93% yield).

Preparation of D-chiroinositol-3-succinate 1,2;5,6-Di-O-isopropylidene-D-chiroinositol-3-succinate (314 mg) was stirred with 80% acetic anhydride at 75° C. for 14 hours. The solution was concentrated to dryness at 35° C. in vacuo and then under high vacuum (500 mTorr) for 24 hours to yield a pure product weighing 244 mg (100% yield).

Preparation of 1,2,4,5,6-penta-O-acetyl-O-chiroinositol-3-succinate

D-chiroinositol-3-succinate (244 mg) was stirred with dry pyridine (5 ml) and dry acetic anhydride (5 ml) at room temperature for 14 hours. The solution was diluted with 50 ml ethyl acetate and washed with 3×25 ml 1N HCl, 10 ml $H_2O$, 10 ml brine, dried over sodium sulfate filtered and ethyl acetate was removed in vacuo. The residue was loaded on a 2×20 cm flash column packed with silica gel 60 and the column was eluted with ethyl acetate until the requisite compound was eluted. The solvent was removed in vacuo to yield 316 mg of the product (74% yield).

Preparation of N-(1,2,4,5,6-penta-O-acetyl-D-chiroinositol-3-succinate)-succinimide (activated ester of PASI)

1,2,4,5,6-Penta-O-acetyl-D-chiroinositol-3-succinate (33.3 mg) was dissolved in 2 ml of dry methylene chloride where 7.8 mg of N-hydroxysuccinimide (NHS) and 14 mg of dicyclohexylcarbodiimide (DCC) was added and stirred at room temperature for 12 hours. The mixture was filtered and the filtrate was dried in vacuo. The residue was loaded on a 2×20 cm flash column packed with silica gel 60 and the column was eluted with 150 ml ether and 5% methanol in ether. The requisite fractions were contained in the 5% methanol in ether eluant. The fractions were combined and the solvents were removed in vacuo to yield 28 mg of the product (70% yield).

Conjugation of the Activated Ester of PASI to BSA

A preparation of NHS-activated PASI was dried overnight under high vacuum (500 mTorr) and then weighed for a total yield of 29 mg. The entire preparation was dissolved in 1.7 ml of dry dimethylformamide (DMF), some of which was then used for conjugation to BSA and the rest saved for ligand synthesis.

In the conjugation of the NHS derivative with BSA, 10 mg of the derivative in 0.6 ml of DMF was combined with 48 mg of BSA in 6 ml of phospho-buffered saline (PBS), pH 7.5, for an input mole ratio of 20:1. Another 0.6 ml of DMF was added to the reaction mix to ensure dissolution of the NHS derivative and the reaction mix was stirred for 5 hours at room temperature. Afterwards dialysis versus PBS, pH 6.5 with 10 percent DMF was started and continued overnight at room temperature, using spectrapor 3 tubing with a 3500 M.W. cutoff.

Percent incorporation was determined by counting $C^{14}$ cpm's which are given below before and after dialysis for both the conjugate reaction mix and a blank reaction mix (no BSA) which was run to access retention of the NHS derivative by itself such as by absorption or precipitation, inside the dialysis tube:

blank before dialysis: 6960 blank after dialysis: 2112 percent retention: 30% conjugate before dialysis: 43200 conjugate after dialysis: 27072 percent retention: 63%

The net retention (conjugate minus blank) was 33%. From this it was calculated that 6.6 mol of inositol was conjugated/mol of BSA.

Preparation of 1,2-O-cyclohexylidenemyoinositol

In a round-bottomed flask fitted with a Dean-Stark adapter and reflux condenser, 2.5 g of myoinositol, 25 ml of cyclohexanone, and 6.5 ml of benzene were added and the mixture was refluxed for 1 hour. p-Toluenesulfonic acid (25 mg) was added and the mixture was refluxed until it became homogenous (5 hours). The solution was cooled to room temperature and the benzene was decanted off. Two more 10 ml decantations with benzene were combined with the reaction decantation, as well as 10 ml of benzene, 15 ml of petroleum ether and 2 ml of ethanol. The mixture was seeded with the product, stirred rapidly for 10 minutes and placed in the −20° C. freezer overnight. Triethylamine (0.2 ml) was added and the crystals were suction filtered and recrystallized from isopropanol to yield 2.71 g (75%) of product.

Preparation 1,2-0-cyclohexylidene-3,4-tetraisopropyldisiloxylmyoinositol 1,2-0-Cyclohexylidenemyoinositol (200 mg) was stirred with 5 ml of dry pyridine. Dichlorotetraisopropyldisiloxane (0.29 ml) was added dropwise and the solution was stirred at room temperature overnight. The solution was diluted with 50 ml of ether and the ether was washed with 2×20 ml of 1N hydrochloric acid, 20 ml of water, 20 ml of brine. The ether was dried over sodium sulfate, filtered and the ether removed in vacuo. The crude material was loaded on a 1×20 cm flash column packed with silica gel 60 and the column was eluted with 3:1 petroleum ether:ethyl acetate. The requisite fractions were combined and the solvents were removed in vacuo to yield 358 mg (93%) of product.

The remainder of the protocol for the preparation of the myoinositol-BSA conjugate (i.e., succinylation, hydrolysis, acetylation, NHS activation, BSA conjugation) is a duplicate of the analogous DCI protocol.

Furthermore, the abbreviation, PASI, refers to the peracetylated succinyl myoinositol as well as the analogous D-chiroinositol.

GENERATION OF ANTIBODIES

The myoinositol-BSA conjugate was used to generate antibodies in the following manner. The BSA conjugate solution was divided into 24 equal portions, lyophilized in vials and sent to Hazelton Research Products, Inc. for injection into 3 rabbits, with 8 boosts/rabbit. Each portion contained approximately 2 mg BSA with 74 ug of inositol derivative. One hundred mg was injected into rabbits at 3 week intervals. The resulting immune sera were tested by ELISA and RIA.

In order to screen immune sera by ELISA, the activated ester of PASI was conjugated to polylysine-20,000 (6.6 mol/mol) and the conjugate (0.02 ug/ml with 0.2 ug/ml unconjugated polylysine) used to coat microtiter wells. Samples were detected by competitive ELISA using goat anti-rabbit-peroxidase conjugate. To prepare a radioligand for RIA, PASI was conjugated to tyramine using DCC. The product was purified by flash chromatography over silica gel and C-18 HPLC, radioiodinated in the presence of chloramine T, and the monoiodinated product purified by HPLC.

PREPARATION OF SAMPLE TO BE ANALYZED

Figure 2:
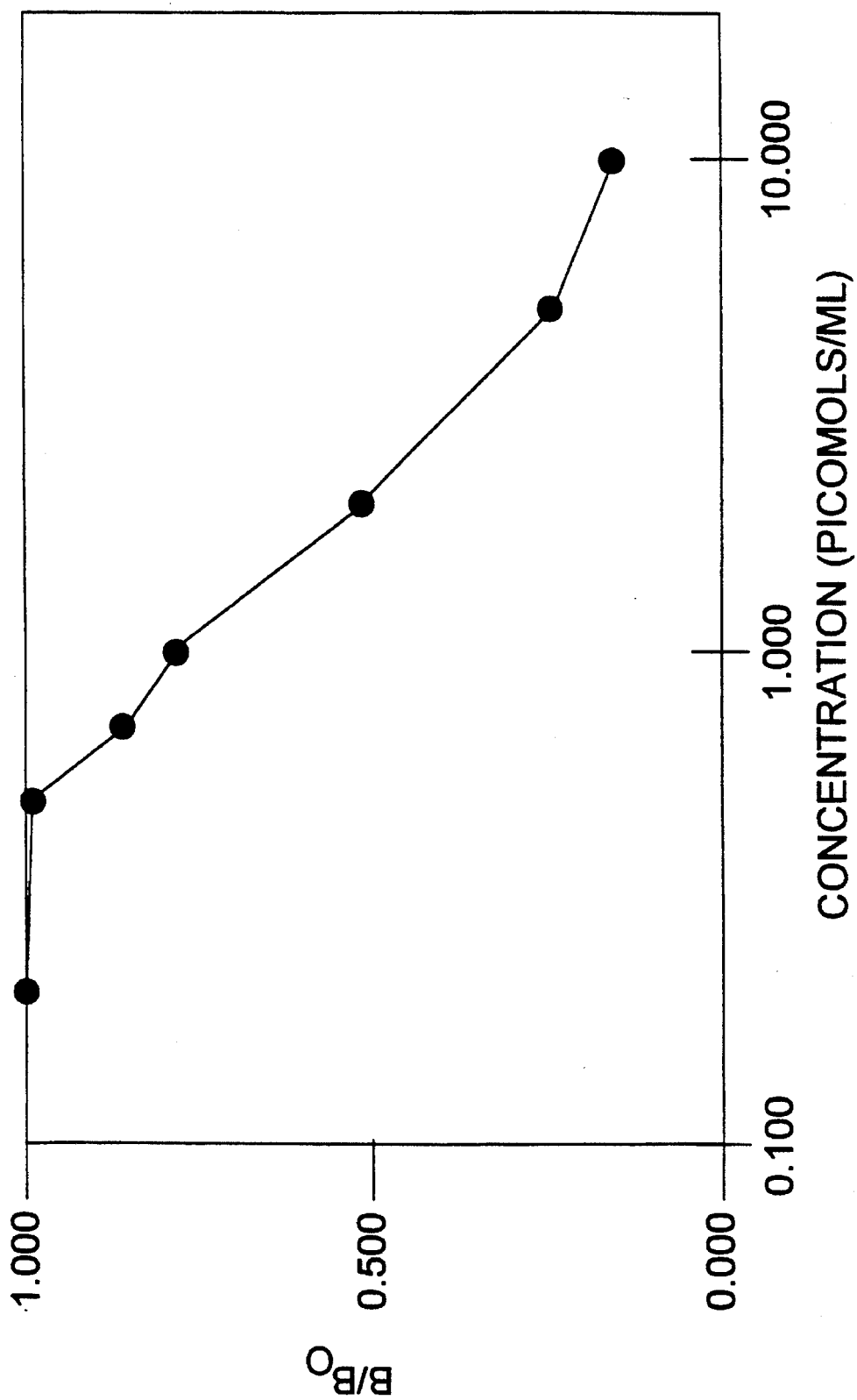
FIG. 2 is a standard assay curve for acetylated chiroinositol.

A typical sample may be from urine or blood. The samples are diluted in phosphate buffered saline 5-fold or more and dried at 60° C. in a Speed-Vac. A 1:1 mixture of pyridine and acetic anhydride is added and the mixture incubated at room temperature overnight and dried on a Speed-Vac at 45° C. Alternatively, the sample may be incubated with 1% sulphuric acid in acetic anhydride at 60° C. for 2 hours. Predrying before incubation is optional. After treatment by either method, the sample is taken up in 50 volumes of PBS or imidazole buffer to 1 ml of volume: aliquots are then assayed by ELISA or RIA. FIG. 1 gives the assay standard curve for totally acetylated myoinositol and indicates a sensitivity of the order of 0.5 picomols/ml. FIG. 2 gives the corresponding assay curve for chiroinositol, showing that both immunoassays achieve similar sensitivities.

Figure 3:
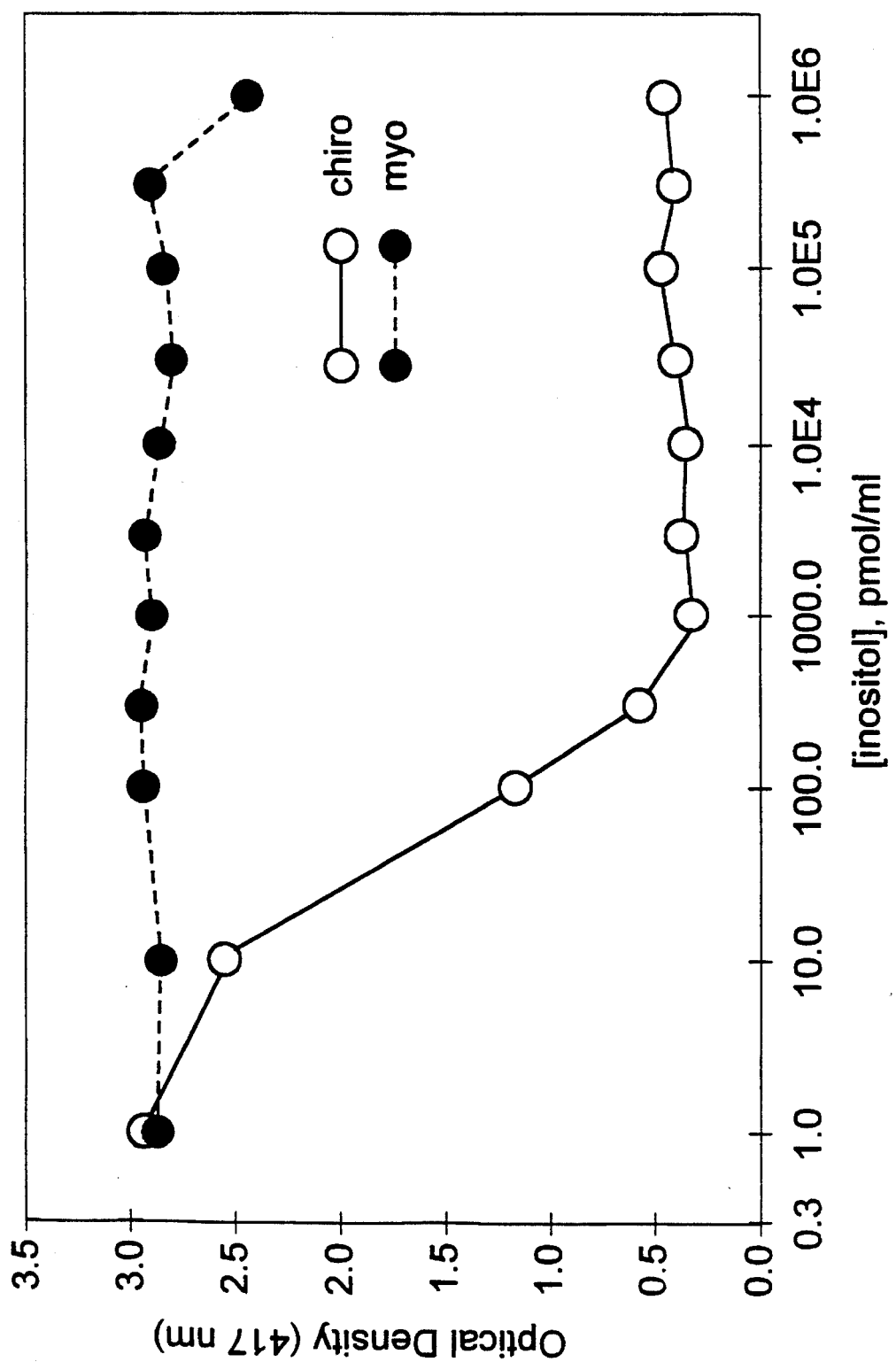
FIG. 3 shows the results of an ELISA performed with antibodies raised against D-chiroinositol.
Figure 4:
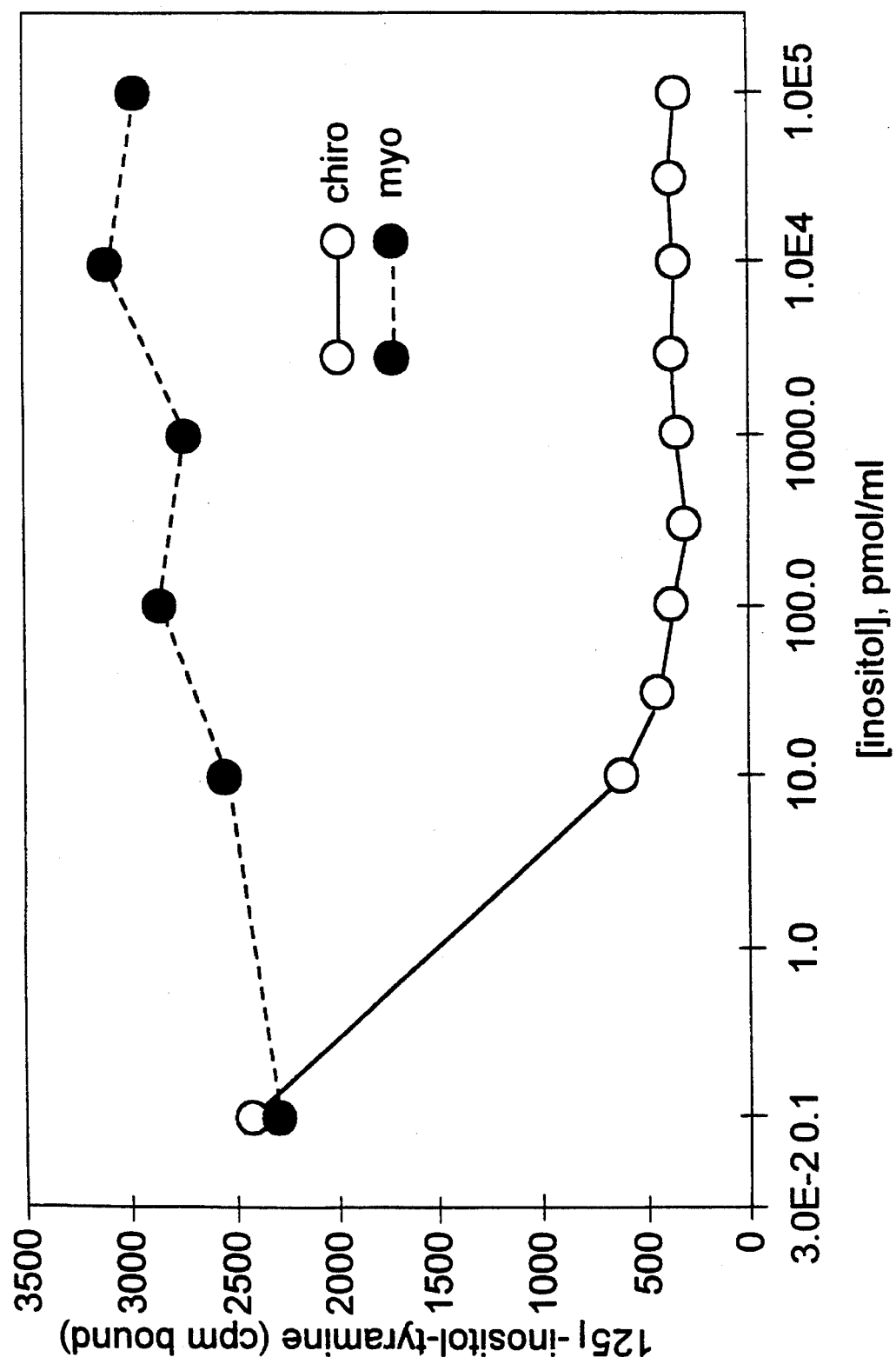
FIG. 4 shows the results of a RIA performed with antibodies raised against myoinositol.

The results of an ELISA performed with antibodies raised against DCI are shown in FIG. 3. Note the high binding affinity for derivatives of DCI and the very low cross reactivity with the derivatives of other isomers of inositol. The results of an RIA for myoinositol performed with the antibodies raised against myoinositol is shown in FIG. 4.

Figure 5:
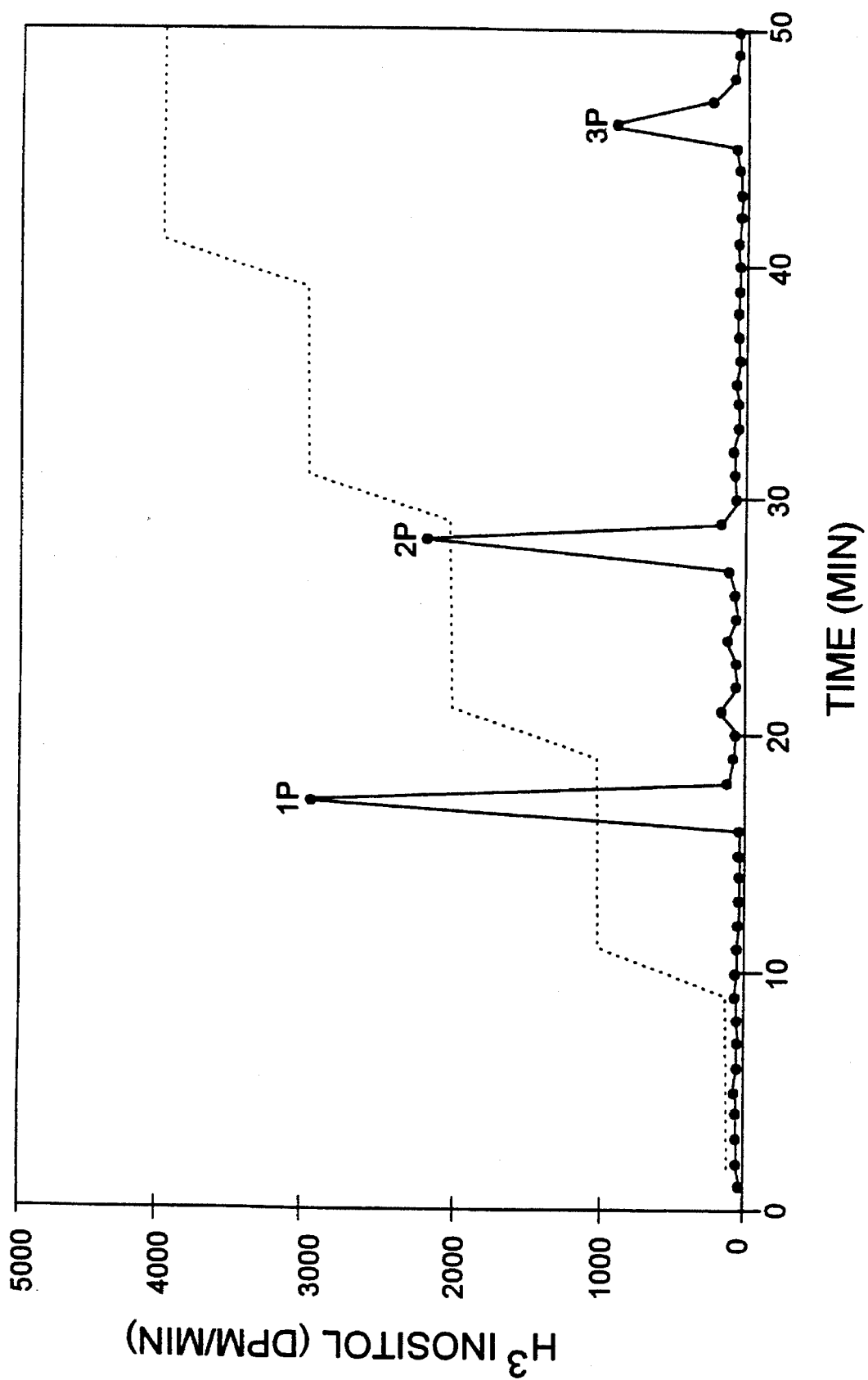
FIG. 5 shows the results of a chromatographic separation of a mixture of mono-, di-, and triphosphates of myoinositol.
Figure 6:
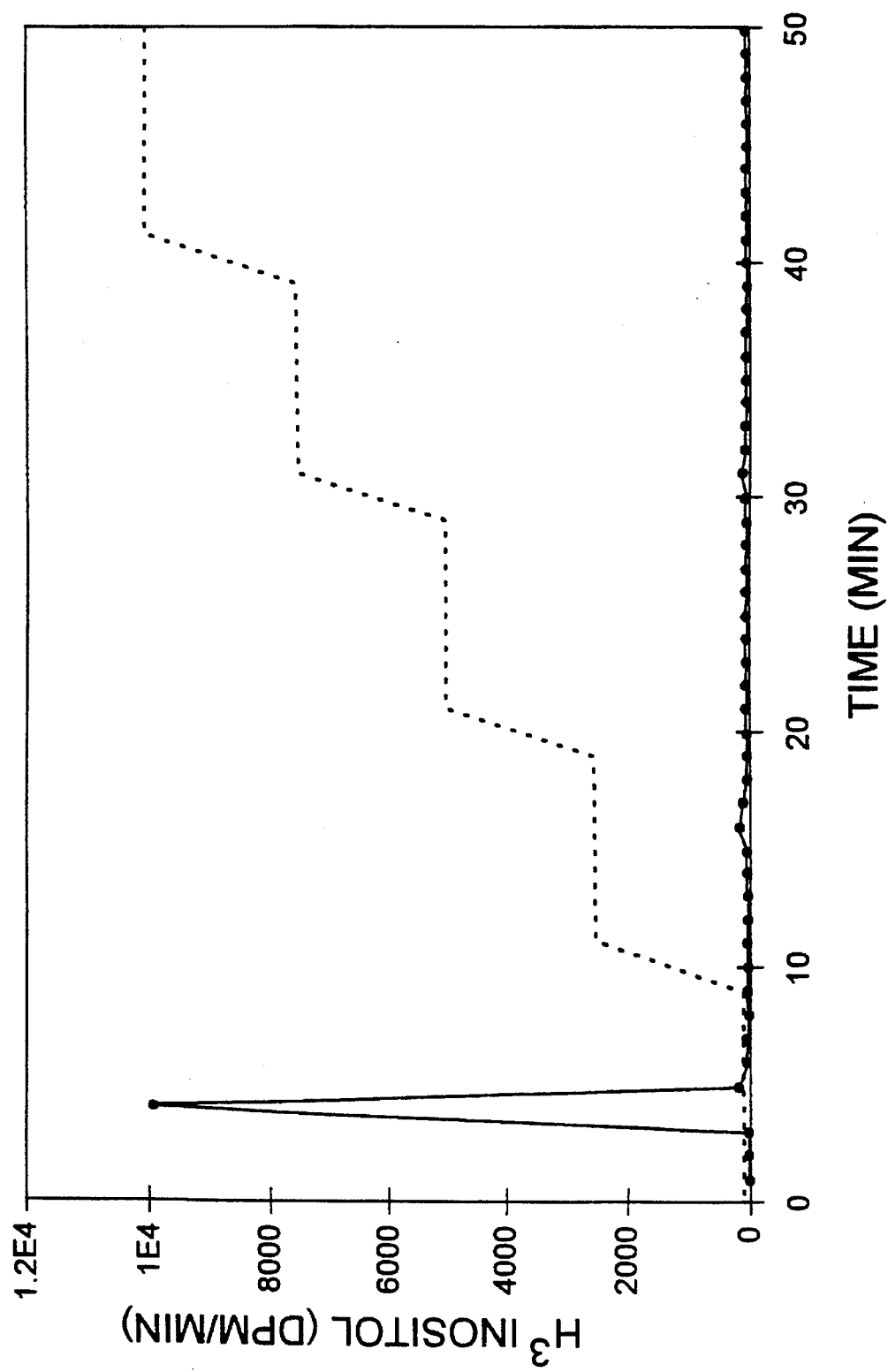
FIG. 6 shows the results of a control hydrolysis of mono-, di-, and triphosphates of myoinositol.

This method may also be used to assay for inositol phosphates. This can be accomplished by hydrolyzing the inositol phosphate to inositol by use of, for example, alkaline phosphatase and then subjecting the inositol to a procedure such as is described above. FIG. 5 shows the results of a chromatographic separation of a mixture of mono-, di-, and triphosphates of myoinositol. These peaks may be hydrolyzed separately or hydrolyzed together to essentially 100% myoinositol. FIG. 6 shows the results of such a control hydrolysis.

We claim:

1. An assay for inositol or inositol containing compounds in a sample, comprising the steps of:
   a. derivatizing the inositol by reacting it with a compound selected from the group consisting of acetals, ketals, aldehydes, alkyl halides, silyl halides, ketones, acid anhydrides, and carboxylic acids;
   b. reacting the sample with an antibody preparation which is specific for the derivatized inositol to form an antibody-derivatized inositol complex;
   c. detecting the presence of the antibody-derivatized inositol complex; and
   d. correlating the detection of the antibody-derivatized inositol complex with the presence of inositol or inositol containing compound in the sample.

2. The assay of claim 1, wherein the derivatized inositol is hexa-O-acetylinositol.

3. An assay for a specific isomer of inositol in a sample, comprising the steps of:
   a. acetylating the inositol isomer;
   b. reacting the sample with an antibody which is specific for the acetylated inositol isomer to form an antibody-acetylated inositol complex;
   c. detecting the presence of the antibody-acetylated inositol complex; and
   d. correlating the detection of the antibody-derivatized inositol complex with the presence of the inositol isomer in the sample.

4. The assay of claim 3, wherein the inositol isomer is D-chiro-inositol.

5. The assay of claim 3, wherein the inositol isomer is myoinositol.

6. The assay of claim 3 wherein all of the hydroxyl groups of the inositol are acetylated.

7. A method for the production of antibodies to inositol, comprising the steps of:
   a. forming an inositol derivative, said inositol derivative being formed by the reaction of inositol and a member selected from the group consisting of acid anhydrides, acetals, ketals, ketones, alkyl halides, carboxylic acids, aldehydes and silyl halides;
   b. linking the inositol derivative to a larger molecule to form an immunogenic conjugate;
   c. exposing an immunologically competent animal to the immunogenic conjugate and allowing the animal to produce antibodies to the immunogenic conjugate; and
   d. collecting the antibodies produced by the animal.

8. The method of claim 7, wherein the inositol derivative is penta-O-acetylinositol.

9. The method of claim 7, wherein the inositol derivative is linked to the larger molecule by a member selected from the group consisting of carboxylic acids, carboxylic acid anhydrides, levulinic acids, pyruvic acids, succinic acids, sulfhydryls and amines.

10. The method of claim 7, wherein the inositol derivative is linked to the larger molecule by a member selected from the group consisting of carboxylic acids and derivatives of carboxylic acids.

11. The method of claim 7 wherein the linker is selected from the group consisting of succinic acid and derivatives of succinic acid.

12. A method for the production of antibodies which bind specifically to a particular isomer of inositol, comprising the steps of:
   a. forming a derivative of the inositol isomer, said derivative being formed by the reaction of the inositol isomer and a member selected from the group consisting of, acetals, ketals, ketones, aldehydes, acid anhydrides, carboxylic acids, alkyl halides, and silyl halides;
   b. linking the derivative to a larger molecule to form an immunogenic conjugate;
   c. exposing an immunologically competent animal to the immunogenic conjugate and allowing the animal to produce antibodies to the immunogenic conjugate; and
   d. collecting the antibodies produced by the animal.

13. The method of claim 12, wherein the derivative is penta-O-acetyl-D-chiroinositol.

14. The method of claim 12 wherein the derivative is penta-O-acetyl myoinositol.

15. The method of claim 12, wherein the inositol derivative is linked to the larger molecule by a member selected from the group consisting of carboxylic acids, carboxylic acid anhydrides, levulinic acids, pyruvic acids, succinic acid, sulfhydryls and amines and derivatives thereof.

16. The method of claim 12, wherein the inositol derivative is linked to the larger molecule by a member selected from the group consisting of carboxylic acids and derivatives thereof.

17. The method of claim 13, wherein the inositol derivative is linked to the larger molecule by a member selected from the group consisting of succinic acid and derivatives thereof.

18. Antibodies produced by the method of claim 12, 13, 14, 15, 16 or 17.

19. Antibodies which bind specifically to derivatives of inositol selected from the group consisting of ethers, acetals, ketals, ketones, acetylated derivatives and acylated derivatives.

20. Antibodies which bind specifically to derivatives of a particular isomer of inositol selected from the group consisting of ethers, acetals, ketals, ketones, acetylated derivatives and acylated derivatives.

21. Antibodies of claim 20, wherein the derivative is an acetylated derivative.

22. Antibodies of claim 21, wherein five of the hydroxy groups of the inositol isomer are acetylated.

* * * * *